(12) United States Patent
Chrisp (10) Patent No.: US 7,041,979 B2
(45) Date of Patent: *May 9, 2006

(54) COMPACT REFLECTIVE IMAGING SPECTROMETER UTILIZING IMMERSED GRATINGS

(75) Inventor: Michael P. Chrisp, Danville, CA (US)

(73) Assignee: The Regents of the University of California, Oakland, CA (US)

( * ) Notice: Subject to any disclaimer, the term of this patent is extended or adjusted under 35 U.S.C. 154(b) by 415 days.

This patent is subject to a terminal disclaimer.

(21) Appl. No.: 10/658,150

(22) Filed: Sep. 9, 2003

(65) Prior Publication Data

US 2005/0051729 A1    Mar. 10, 2005

(51) Int. Cl.
*G01N 21/35* (2006.01)
(52) U.S. Cl. .................................. 250/339.07
(58) Field of Classification Search ............ 250/339.07
See application file for complete search history.

(56) References Cited

U.S. PATENT DOCUMENTS

| | | |
|---|---|---|
| 5,127,728 A | 7/1992 | Warren et al. |
| 5,717,487 A | 2/1998 | Davies |
| 5,781,290 A | 7/1998 | Bittner et al. |
| 5,880,834 A | 3/1999 | Chrisp |
| 6,016,220 A | 1/2000 | Cook |
| 6,078,048 A | 6/2000 | Stevens et al. |
| 6,100,974 A | 8/2000 | Reininger |
| 6,122,051 A | 9/2000 | Ansley et al. |
| 6,266,140 B1 | 7/2001 | Xiang et al. |
| 6,388,799 B1 | 5/2002 | Arnone et al. |
| 6,538,737 B1 | 3/2003 | Sandstrom et al. |
| 6,813,018 B1 * | 11/2004 | Richman ............... 356/328 |
| 2002/0101587 A1 | 8/2002 | Wilson et al. |
| 2002/0135770 A1 | 9/2002 | Lewis et al. |
| 2003/0016355 A1 | 1/2003 | Koike et al. |
| 2005/0041247 A1 * | 2/2005 | Lerner et al. ............ 356/328 |

FOREIGN PATENT DOCUMENTS

WO    WO 99/63311    12/1999

* cited by examiner

*Primary Examiner*—David Porta
*Assistant Examiner*—Djura Malevic
(74) *Attorney, Agent, or Firm*—Eddie E. Scott; Alan H. Thompson (57) ABSTRACT

A compact imaging spectrometer comprising an entrance slit for directing light, a first mirror that receives said light and reflects said light, an immersive diffraction grating that diffracts said light, a second mirror that focuses said light, and a detector array that receives said focused light. The compact imaging spectrometer can be utilized for remote sensing imaging spectrometers where size and weight are of primary importance.

20 Claims, 4 Drawing Sheets

COMPACT REFLECTIVE IMAGING SPECTROMETER UTILIZING IMMERSED GRATINGS

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to the field of imaging spectrometry, and more particularly to a compact reflective imaging spectrometer.

2. State of Technology

U.S. Pat. No. 5,717,487 issued Feb. 10, 1998 to Donald W. Davies, and assigned to TRW Inc., provides the following state of technology information, "A spectrometer is a known instrument for examining the spectral characteristics of light. Light emitted from or reflected by an object is received within the spectrometer and separated into its spectral components, such as the red, green and blue colored spectra as occurs in equal intensity when standard white light is so analyzed. The intensity of each such spectral component of that received light may be readily observed and measured. Each element of nature, molecular components, organic and inorganic compounds, living plants, man, animal and other substances is known to emit a unique spectrum that may be used as an indicium to identify the emitter. In past scientific work, the spectral analyses of a host of known elements, molecules, materials, living plants, gases and the like, has been compiled into a library. That library enables objects and things to be identified solely by the spectrometric analysis of the light reflected therefrom. Thus, as example, by examining the spectral content of light reflected from the distant planets, astronomers identified the constituent elements, such as iron, forming those planets; by examining the spectral content of Gases emitted by factory smokestacks, scientists determine if pollutants are being emitted in violation of law or regulation; by examining the spectral content of land, the environmental engineer is able to determine the botanical fertility of a region and its mineral content, and, with subsequent observations, to determine the change in the environment with time; and by examining the spectral content of light reflected in multiple scans over a geographic region, military personnel identify camouflaged military equipment, separate from plant life, in that geographic region. The foregoing represent but a small number of the many known uses of this useful scientific tool."

United States Patent Application No. 20020135770 published Sep. 26, 2003 by E. Neil Lewis and Kenneth S. Haber for a Hybrid Imaging Spectrometer, provides the following state of technology information, "Imaging spectrometers have been applied to a variety of disciplines, such as the detection of defects in industrial processes, satellite imaging, and laboratory research. These instruments detect radiation from a sample and process the resulting signal to obtain and present an image of the sample that includes spectral and chemical information about the sample."

U.S. Pat. No. 6,078,048 issued Jun. 20, 2000 to Charles G. Stevens and Norman L. Thomas for an immersion echelle spectrograph, assigned to The Regents of the University of California, provides the following state of technology information, "In recent years substantial effort has been directed to the problem of detection of airborne chemicals. The remote detection of airborne chemicals issuing from exhaust stacks, vehicle exhaust, and various exhaust flumes or plumes, offers a non-intrusive means for detecting, monitoring, and attributing pollution source terms. To detect, identify, and quantify a chemical effluent, it is highly desirable to operate at the limiting spectral resolution set by atmospheric pressure broadening at approximately 0.1 cm.sup.−1. This provides for maximum sensitivity to simple molecules with the narrowest spectral features, allows for corrections for the presence of atmospheric constituents, maximizing species selectivity, and provides greater opportunity to detect unanticipated species. Fourier transform spectrometers, such as Michelson interferometers, have long been the instrument of choice for high-resolution spectroscopy in the infrared spectral region. This derives from its advantage in light gathering power and spectral multiplexing over conventional dispersive spectrometers. For remote sensing applications and for those applications in hostile environments, the Fourier transform spectrometer, such as the Michelson interferometer, is ill suited for these applications due to the requirements for keeping a moving mirror aligned to better than a wavelength over the mirror surface. Furthermore, this spectrometer collects amplitude variations over time that are then transformed into frequency information for spectral generation. Consequently, this approach requires stable radiation sources and has difficulty dealing with rapidly changing reflectors or emissions as generally encountered in remote field observations, particularly from moving observation platforms. Furthermore, under conditions where the noise terms are dominated by the light source itself, the sensitivity of the instrument is limited by the so-called multiplex disadvantage."

U.S. Pat. No. 5,880,834 issued Mar. 9, 1999 to Michael Peter Chrisp for a convex diffraction grating imaging spectrometer, assigned to The United States of America as represented by the Administrator of the National Aeronautics and Space Administration, provides the following state of technology information, "There are three problems in designing an imaging spectrometer where light in a slice of an image field passing through an entrance slit is to be diffracted by a grating parallel to the slit and imaged onto a focal plane for display or recording with good spatial resolution parallel to the slit and good spectral resolution perpendicular to the slit: 1. Eliminating astigmatism over the spectrum on the image plane. 2. Removing field curvature from the spectrum focused onto the image plane. 3. Obtaining good spatial resolution of the entrance slit which involves eliminating astigmatism at different field angles from points on the entrance slit."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a compact imaging spectrometer utilizing mirrors and immersive diffraction gratings. In one embodiment the present invention provides a compact reflective imaging spectrometer apparatus comprising an entrance slit for directing light, a first mirror that receives said light and reflects said light, an immersive diffraction grating that diffracts said light, a second mirror that focuses said light, and a detector array that receives said focused light. Imaging spectrometers constructed in accordance with the present invention are can be utilized for remote sensing imaging spectrometers where size and weight are of primary importance. Imaging spectrometers constructed in accordance with the present invention have very good spectral and spatial registration, providing accurate spectral data for algorithm retrievals. This avoids having to resample the images to correct for these defects, which has the disadvantage of creating spectral mixing between pixels, which reduces the sensitivity and accuracy of the retrieval algorithms.

Imaging spectrometers constructed in accordance with the present invention use smaller cryogenic coolers facilitating their use in portable (man carried) remote sensing systems and in small unmanned aerial vehicles. These have application to Homeland Defense. One embodiment of the present invention has the capability to cover multiple butted detector arrays and its principal application would be space based infrared remote sensing. Imaging spectrometers constructed in accordance with the present invention can be used for commercial remote sensing where portability is important. Examples of use of imaging spectrometers constructed in accordance with the present invention include pollution detection, remote sensing of agricultural crops, geological identification, and the remote monitoring of industrial processes. Embodiments of the present invention can be produced in volume at low cost, with diamond turned mirrors and a diamond flycut grating. The precision diamond cut parts will enable a snap together design with little or no alignment.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Referring now to the drawings, to the following detailed description, and to incorporated materials; detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Figure 1:
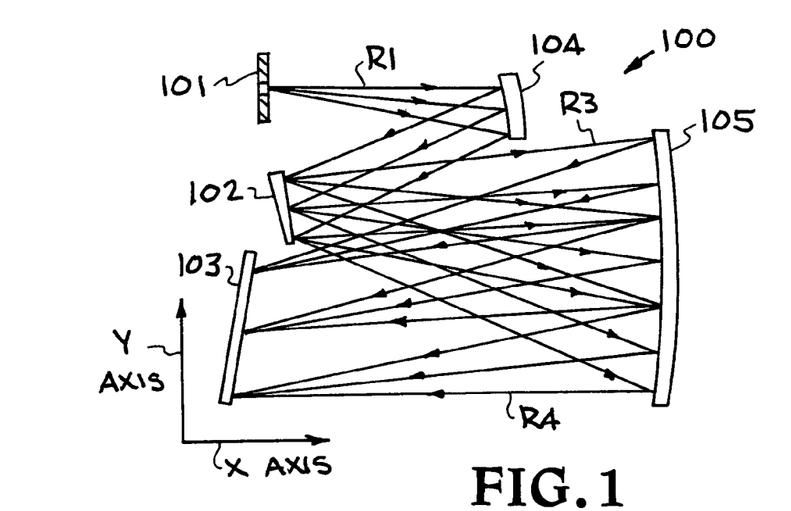
FIG. 1 is a raytrace illustrating an embodiment of a compact imaging spectrometer constructed in accordance with the present invention.

Referring to FIG. 1, an embodiment of a compact imaging spectrometer constructed in accordance with the present invention is illustrated. This embodiment is designated generally by the reference numeral 100. FIG. 1 is a raytrace for the compact imaging spectrometer 100. The embodiment 100 of a compact reflective imaging spectrometer includes a two-dimensional detector array to enable spectral analysis of the spatial structure of objects within the scene.

The structural elements of the compact imaging spectrometer 100 include an entrance slit 101, a germanium or zinc selenide grating 102, an array detector 103, a concave mirror 105, and a concave mirror 106. The compact imaging spectrometer 100 provides an infrared reflective imaging spectrometer apparatus that comprises an entrance slit for directing light, a concave reflective primary mirror for reducing the divergence of said light from said entrance slit, a wedged germanium or zinc selenide grating dispersing said light and a concave reflective secondary mirror focusing said light onto a two-dimensional detector array.

The compact imaging spectrometer 100 provides a small size for the compact imaging spectrometer 100. Small size is extremely important because it determines the requirements for cryogenic cooling and whether the spectrometer can fly in a small UAV or be man portable. The compact imaging spectrometer 100 is smaller than spectrometers currently in use. The reduced cryogenic cooling requirements of the compact imaging spectrometer 100 allow its use in small unmanned aerial vehicles. The reduced cryogenic cooling requirements of the compact imaging spectrometer 100 also allows it to be used for man portable instruments. The compact imaging spectrometer 100 has a size envelope that is smaller than spectrometers currently in use. The entrance slit 101, the first mirror 104, the immersive diffraction grating 102, the second mirror 105, and the detector array 103 fit within the envelope. The envelope is 2.5 cm by 3.2 cm by 2.2 cm or smaller. As shown in FIG. 1 the X axis is 3.2 cm and the Y axis is 2.5 cm and the z-axis 2.2 cm.

The compact imaging spectrometer 100 meets the requirements in Table 1 below.

TABLE 1

(Imaging Spectrometer Performance)

| | |
|---|---|
| Spectral Range | 8–13.5 microns |
| F-number | 5 |
| Detector array | 256 spatial × 256 spectral |

TABLE 1-continued (Imaging Spectrometer Performance)

| Pixel size | 40 microns |
|---|---|
| Entrance slit length | 10.24 mm |
| Spatial distortion: change in spatial mapping with wavelength | <0.1 pixel (<±2 microns) |
| Spectral distortion: spectral smile | <0.1 pixel (<t2 microns) |
| Optical performance | Diffraction limited |

The compact imaging spectrometer 100 is diffraction limited over the wavelength range with excellent spatial and spectral resolution. The spectral slit curvature of the entrance slit 101 has been corrected to less than one tenth of a pixel over the detector arrays. This is the curvature of slit image on the detector at different wavelengths, which is a common problem with imaging spectrometer designs. The spatial mapping distortion has also been corrected to less than one tenth off a pixel over the full wavelength range. This means that the spectrum from a single point in the entrance slit will not wander from the center of a row pixels by less than ±2 microns. Correcting the spectral slit curvature and the spatial mapping distortion with wavelength to less than one tenth of a pixel ensures that the images do not have to be resampled to correct for these distortions.

Figure 7:
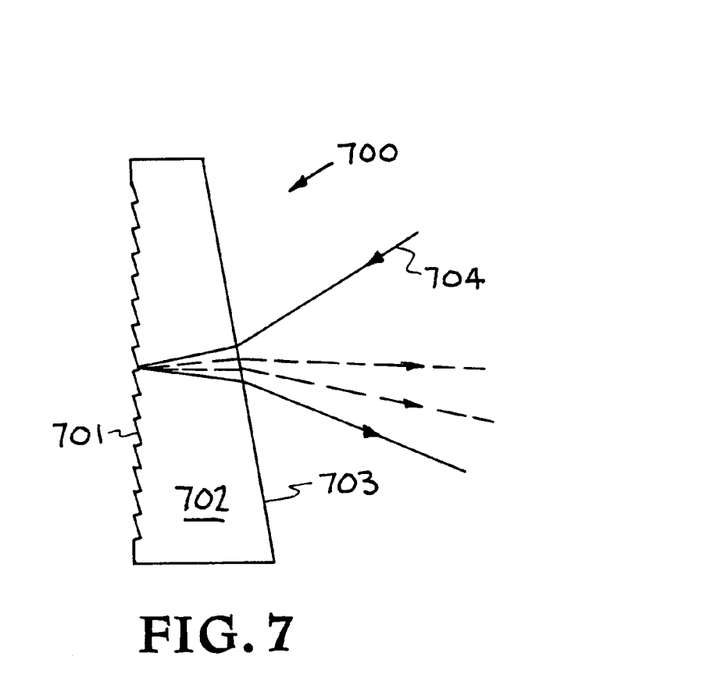
FIG. 7 illustrates the gratings 102, 302 and 502.

The concave mirrors 105 and 106 in the compact imaging spectrometer 100 can be diamond turned and are sections of spheres or rotational aspheres. The germanium or zinc selenide diffraction grating 102 has the rulings immersed into a flat germanium or zinc selenide surface. The grating can be diamond flycut with a blazed profile that will have maximum diffraction efficiency. In the compact imaging spectrometer 100 conventional gratings are used with equally spaced straight rulings. Performance improvement is obtained with curved gratings with varying the ruling spacings. For the diffraction grating, light enters from the front germanium or zinc selenide surface (which usually has power) and then passes through the germanium to diffraction off the grating rulings at the back surface. The diffracted light then propagates through the germanium and out through the front surface (FIG. 7). The grating is cut on the back of a wedged plano-convex or plano-concave lens. In some of these designs the power can be eliminated from the lens resulting in the grating being cut on the back of a wedged germanium prism.

The cold stop in the compact imaging spectrometer 100 is at the germanium or zinc selenide grating. This ensures that the warm back radiation from outside the spectrometer entrance slit does not reach the detector array. This would cause unacceptable degradation in the signal to noise ratio. The geometry of the compact imaging spectrometer 100 allows a transmissive cold stop to be used ahead of the grating, for even better thermal background reduction, but this also increases the grating sizes. The compact imaging spectrometer 100 has approximately unit magnification and is close to telecentric in the object and image spaces. This provides an easy interface to the front-end optical system, and also relaxes the tolerances on positioning the detector while still meeting the distortion requirements.

Figure 2:
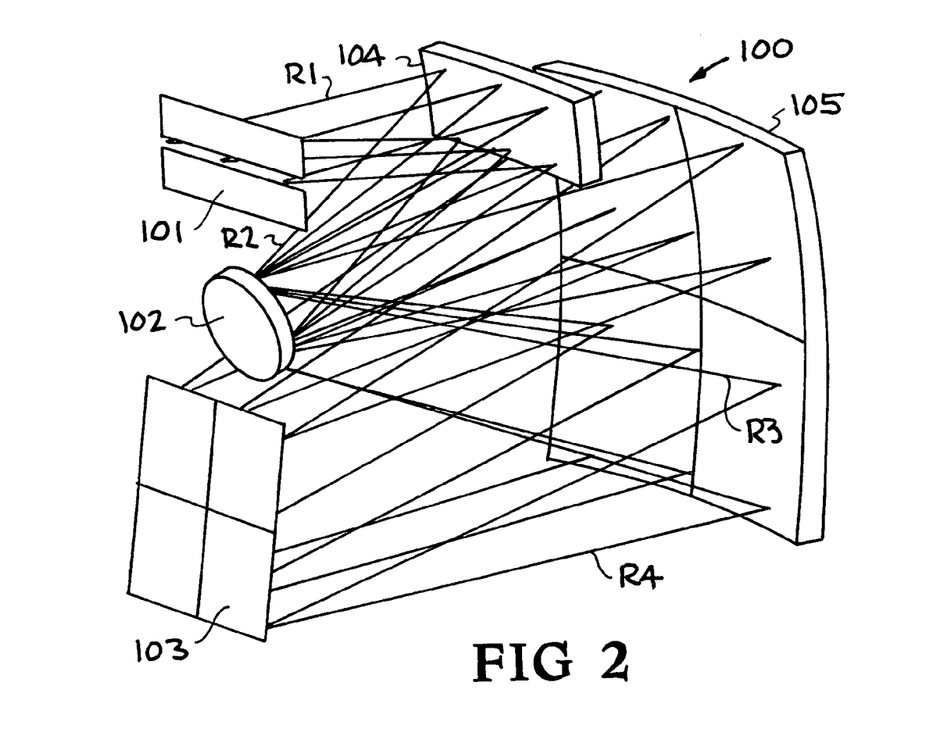
FIG. 2 is a perspective view of the raytrace illustrating an embodiment of a compact imaging spectrometer constructed in accordance with the present invention shown in FIG. 1.

Referring now to FIG. 2, a perspective view of the raytrace for the compact imaging spectrometer 100 is shown. For the compact imaging spectrometer 100 light goes from the entrance slit 101 to the first concave mirror 104, which reflects it to the ruled germanium or zinc selenide grating 102. The diffracted order then propagates to the second mirror 105 that focuses the light onto the 2D detector array 103. The germanium or zinc selenide grating 102 is a wedged plano-concave lens with the grating ruled on the flat side. The grating can be made into a plano-plano wedged prism with some performance degradation.

In operation of the compact imaging spectrometer 100, rays R1 diverge from slit 101. For the compact imaging spectrometer 100 light goes from the entrance slit 101 to the first concave mirror 104, which reflects it to the ruled germanium or zinc selenide grating 102. The diffracted order then propagates to the second mirror 105 that focuses the light onto the 2D detector array 103.

Figure 3:
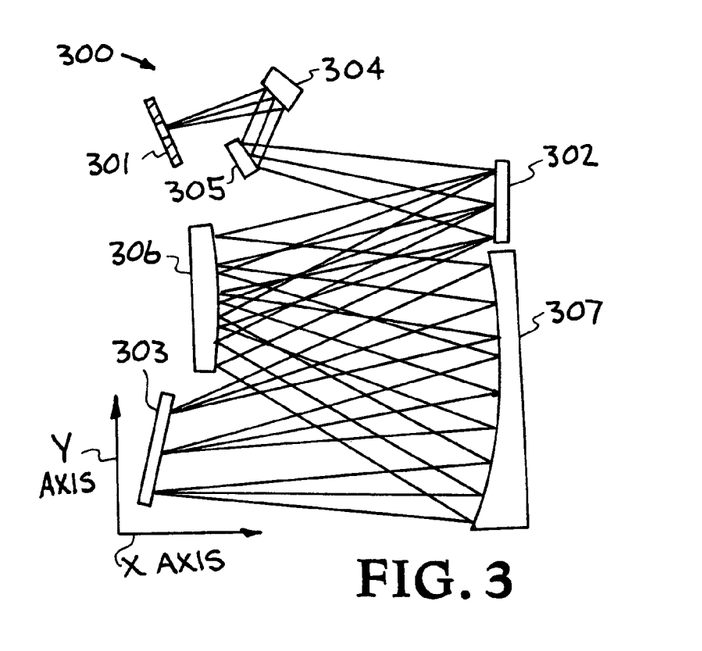
FIG. 3 is a raytrace illustrating another embodiment of a compact imaging spectrometer constructed in accordance with the present invention.

Referring to FIG. 3, another embodiment of a compact imaging spectrometer constructed in accordance with the present invention is illustrated. This embodiment of the present invention is designated generally by the reference numeral 300. FIG. 3 is a raytrace for the compact imaging spectrometer 300.

The infrared reflective imaging spectrometer 300 comprises an entrance slit 301 for directing light, mirrors 304 and 305 for reducing the divergence of the light from the entrance slit 301, a wedged germanium or zinc selenide grating 302 for dispersing the light, a mirror 306 and a concave reflective mirror 307 for focusing the light onto the two-dimensional detector array 303. The concave reflective primary 304 and the concave reflective mirror 307 have conic sections or rotational aspheric sections or toric sections. The wedged germanium or zinc selenide grating 303 has a wedge angle that provides slit curvature correction. In one embodiment, the wedged germanium or zinc selenide grating 303 is a conventional straight grooved grating. In another embodiment the wedged germanium or zinc selenide grating 303 is a holographic grating that provides further aberration and distortion correction. In another embodiment the wedged germanium or zinc selenide grating 303 is a diffraction grating with non-uniform groove spacings. In another embodiment the wedged germanium or zinc selenide grating 303 is a diffraction grating with curved groove spacings that provide further aberration and distortion correction. In another embodiment the wedged germanium or zinc selenide grating 303 has power added to surfaces of the wedged grating for greater distortion and field curvature correction. In another embodiment the wedged germanium or zinc selenide grating 303 includes a lens added in front of the detector array to control the field curvature.

Figure 4:
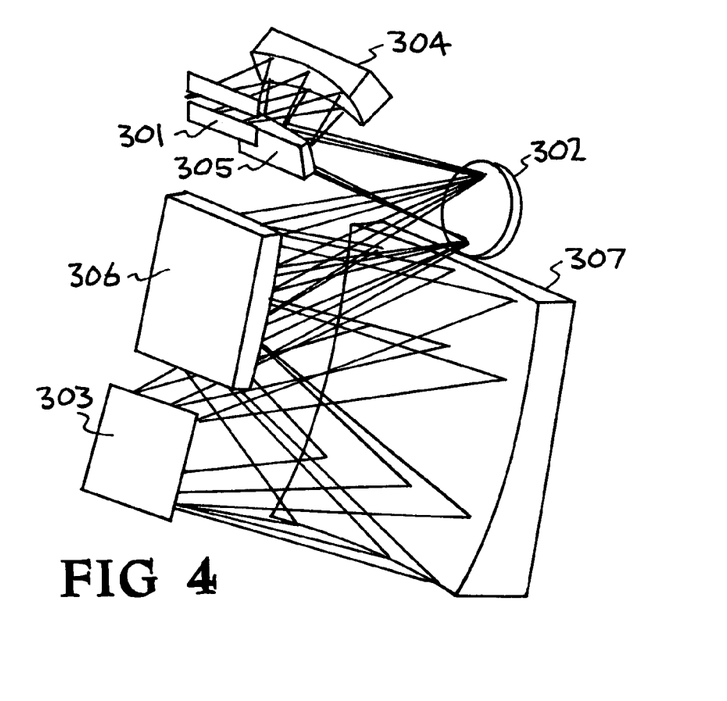
FIG. 4 is a perspective view of the raytrace illustrating the embodiment of a compact imaging spectrometer constructed in accordance with the present invention shown in FIG. 4.

Referring now to FIG. 4, a perspective view of the raytrace for the compact imaging spectrometer 300 is shown. In the compact imaging spectrometer 300, the two mirrors 304 and 305 are ahead of the grating 302. The grating 302 is cut into the flat side of a plano-convex lens. After the grating 302 the mirror 306 and concave mirror 307 focus the light onto the detector array 303. For the compact imaging spectrometer 300 light goes from the entrance slit 301 to the mirrors 304 and 305 which reflects it to the ruled germanium or zinc selenide grating 302. The diffracted order then propagates to the mirror 306 and concave mirror 307 that focuses the light onto the 2D detector array 303. All the requirements in Table 1 are met.

Figure 5:
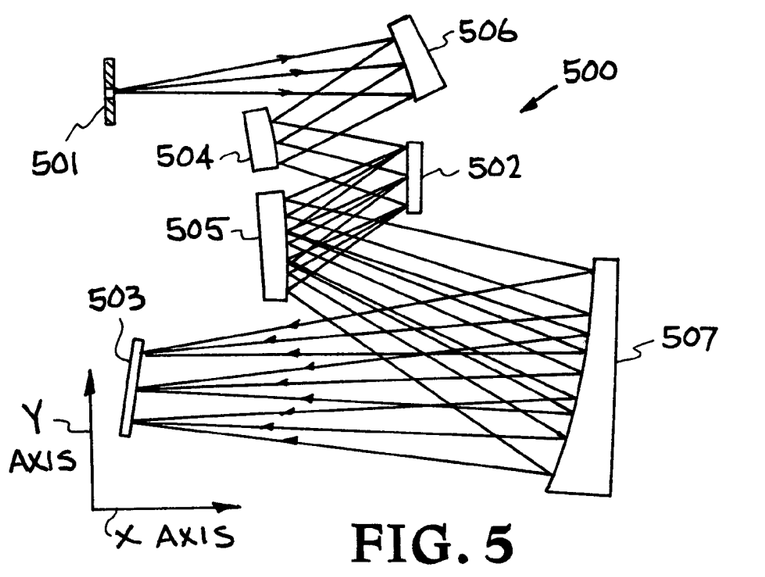
FIG. 5 is a raytrace illustrating yet another embodiment of a compact imaging spectrometer constructed in accordance with the present invention.

Referring to FIG. 5, yet another embodiment of a compact imaging spectrometer constructed in accordance with the present invention is illustrated. This embodiment of the present invention is designated generally by the reference numeral 500. FIG. 5 is a raytrace for the compact imaging spectrometer 500. The structural elements of the compact imaging spectrometer 500 include an entrance slit 501, a germanium or zinc selenide grating 502, an array detector 503, mirrors 504 & 505, and concave mirrors 506 & 507

Figure 6:
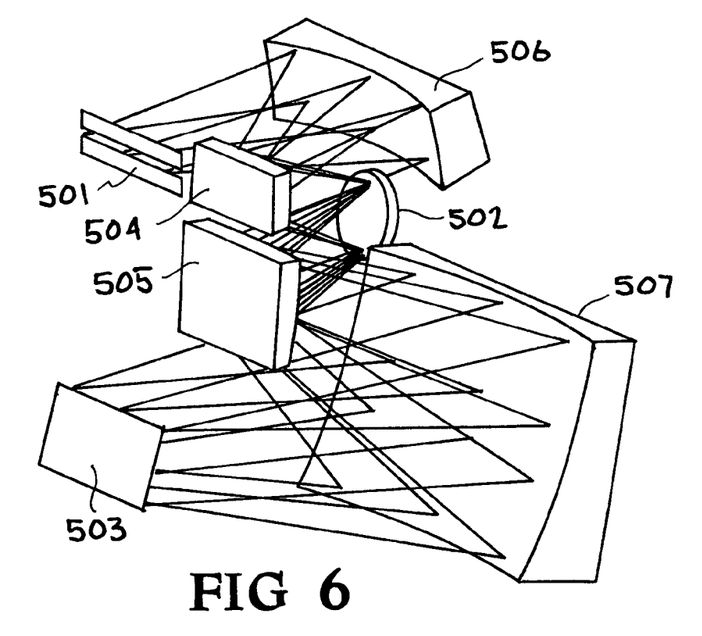
FIG. 6 is a perspective view of the raytrace illustrating the embodiment of a compact imaging spectrometer constructed in accordance with the present invention shown in FIG. 5.

Referring now to FIG. 6, a perspective view of the raytrace for the compact imaging spectrometer 500 is shown. The compact imaging spectrometer 500 is a four mirror design with a wedged plano-convex grating 502. For the compact imaging spectrometer 500 light goes from the entrance slit 501 to the mirrors 506 and 504, which reflects it to the ruled germanium or zinc selenide grating 502. The diffracted order then propagates to mirror 505 and the concave mirror 507 that focuses the light onto the 2D detector array 503.

The compact imaging spectrometer 500 exceeds the requirements in Table 1 and is designed for diffraction imaging operation with distortion correction over larger array sizes than spectrometers 100 and 300. The compact imaging spectrometer 500 can cover spatially three 256×256 40 micron detector arrays to give a wide spatial entrance slit. Without much increase in size, the performance can be extended to six 256×256 detector arrays butted together to give 512 spectral pixels by 768 spatial pixels. The application for this embodiment is space based and aircraft remote sensing systems using next generation infrared detector arrays which are buttable.

Referring now to FIG. 7, details of the gratings 102, 302 and 502 are illustrated. The gratings 102, 302 and 502 are represented by the grating designated generally by the reference numeral 700. The germanium or zinc selenide diffraction grating has the rulings 701 immersed into a flat germanium or zinc selenide surface.

The grating 700 can be diamond flycut with a blazed profile that will have maximum diffraction efficiency. In some embodiments of the compact imaging spectrometers 100, 300, and 500, conventional gratings are used with equally spaced straight rulings. Performance improvement is obtained with curved gratings with varying the ruling spacings. For the diffraction grating 700, light 704 enters from the front germanium or zinc selenide surface 703 (which usually has power) and then passes through the substrate material 702 to diffract off the grating rulings 701 on the back surface. The diffracted light then propagates back through the substrate material germanium and out through the front surface.

The front surface 703 can have power for additional aberration and field curvature correction. In some of these designs the power can be eliminated from the front surface resulting in the grating being cut on the back of a wedged germanium or zinc selenide prism. The wedge angle of the wedged substrate provides slit curvature. In one embodiment, the wedged germanium or zinc selenide grating is a conventional straight grooved grating. In another embodiment the wedged germanium or zinc selenide grating is a holographic grating that provides further aberration and distortion correction. In another embodiment the wedged germanium or zinc selenide grating is a diffraction grating with non-uniform groove spacings. In another embodiment the wedged germanium or zinc selenide grating is a diffraction grating with curved groove spacings that provide further aberration and distortion correction. In another embodiment the wedged germanium or zinc selenide grating has power added to surfaces of the wedged grating for greater distortion and field curvature correction. In another embodiment of the wedged germanium or zinc selenide grating, optical materials for the wedged grating substrate are materials that transmit visible light for operation in the visible spectral region.

Other embodiments of the infrared reflective imaging spectrometer of the present invention include the use of other optical materials 702 for the wedged grating that are substituted for the wedged germanium or zinc selenide grating to enhance the transmittance in the near, mid or long wave infrared regions. In the other embodiments, the optical materials for the wedged grating are known materials that transmit visible light for operation in the visible spectral region.

In one embodiment, the wedged germanium or zinc selenide grating 700 is a holographic grating that provides further aberration and distortion correction. In another embodiment of the present invention, power is added to surfaces of the wedged grating for greater distortion and field curvature correction. In another embodiment of the present invention, a lens is added in front of the detector array to control the field curvature.

Figure 8:
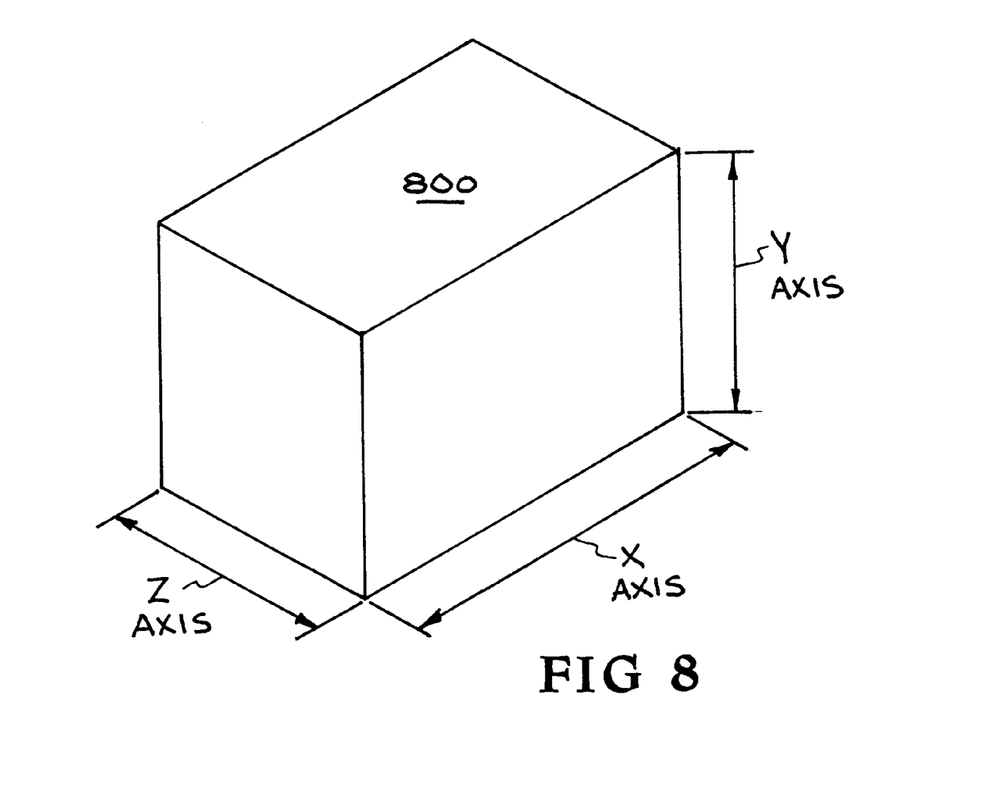
FIG. 8 illustrates the envelope of the spectrometer.

Referring now to FIG. 8, the envelope of the spectrometers 100, 300, and 500 will be illustrated. The envelope is designated generally by the reference numeral 800. The compact imaging spectrometers 100, 300, and 500 have a front and a back. The entrance slit and detector array are located at or near the font. The second mirror that focuses said light is located at or near the back. The entrance slit, first mirror, immersive diffraction grating, second mirror, and detector array fits within an envelope located between the front and back.

With regard to the spectrometer 100, the entrance slit 101, the first mirror 104, the immersive diffraction grating 102, the second mirror 105, and the detector array 103 fit within the envelope 800. The envelope for spectrometer 100 is 2.5 cm by 3.5 cm by 2.2 cm or smaller. As shown in FIG. 8 the X axis is 3.5 cm, the Y axis is 2.5 cm, and the Z axis 2.2.

With regard to the spectrometer 300, the entrance slit 301, mirrors 304, 305, and 306, the immersive diffraction grating 302, the concave mirror 307, and the detector array 303 fit within the envelope 800. The envelope for spectrometer 300 is 5.2 cm by 5 cm by 3.6 cm or smaller. As shown in FIG. 8 the X axis is 5 cm, the Y axis is 5.2 cm, and the Z axis 3.6 cm.

With regard to the spectrometer 500, the entrance slit 301, mirrors 304, 305, and 306, the immersive diffraction grating 302, the concave mirror 307, and the detector array 303 fit within the envelope 800. The envelope for spectrometer 300 is 7 cm by 7.5 cm by 5 cm or smaller. As shown in FIG. 8 the X axis is 7.5 cm, the Y axis is 7 cm, and the Z axis 5 cm.

The envelope 800 provides a small size for the spectrometers 100, 300, and 500. Small size is extremely important because it determines the requirements for cryogenic cooling and whether the spectrometer can fly in a small UAV or be man portable. The compact imaging spectrometers 100, 300, and 500 are smaller than spectrometers currently in use. The reduced cryogenic cooling requirements of the compact imaging spectrometers 100, 300, and 500 allow their use in small, unmanned aerial vehicles. The reduced cryogenic cooling requirements of the compact imaging spectrometers 100, 300, and 500 also allows them to be used for man portable instruments.

Other embodiments of the infrared reflective imaging spectrometer of the present invention include the use of other optical materials for the wedged grating that are substituted for the wedged germanium or zinc selenide grating to enhance the transmittance in the near, mid or long wave infrared regions. In the other embodiments, the optical materials for the wedged grating are known materials that transmit visible light for operation in the visible spectral region.

In one embodiment of the present invention, the wedged germanium or zinc selenide grating is a holographic grating that provides further aberration and distortion correction. In another embodiment of the present invention, power is added to surfaces of the wedged grating for greater distortion and field curvature correction. In another embodiment of the present invention, a lens is added in front of the detector array to control the field curvature.

Imaging spectrometers constructed in accordance with the present invention use smaller cryogenic coolers facilitating their use in portable (man carried) remote sensing systems and in small unmanned aerial vehicles. These have application to Homeland Defense. One embodiment of the present invention has the capability to cover multiple butted detector arrays and its principal application would be space based infrared remote sensing. Imaging spectrometers constructed in accordance with the present invention can be used for commercial remote sensing where portability is important. Examples of use of imaging spectrometers constructed in accordance with the present invention include pollution detection, remote sensing of agricultural crops, geological identification, and the remote monitoring of industrial processes. Embodiments of the present invention can be produced in volume at low cost, with diamond turned mirrors and a diamond flycut grating. The precision diamond cut parts will enable a snap together design with little or no alignment.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A compact imaging spectrometer apparatus, comprising:
   an entrance slit for directing light,
   a first mirror that receives said light and reflects said light,
   an immersive diffraction grating that diffracts said light, wherein said immersive diffraction grating has rulings that are cut on the plano side of a wedged plano-convex or plano-concave lens,
   a second mirror that focuses said light, and
   a detector array that receives said focused light.

2. A compact imaging spectrometer apparatus, comprising:
   an entrance slit for directing light,
   a first mirror that receives said light and reflects said light,
   an immersive diffraction grating that diffracts said light,
   a second mirror that focuses said light, and
   a detector array that receives said focused light,
   wherein said apparatus has a front and a back, and wherein said entrance slit and said detector array are located at or near said front, and wherein said second mirror that focuses said light is located at or near said back.

3. An infrared reflective imaging spectrometer apparatus, comprising:
   an entrance slit for directing light,
   a concave reflective primary mirror for reducing the divergence of said light from said entrance slit,
   a wedged germanium or zinc selenide immersed grating dispersing said light, wherein said wedged germanium or zinc selenide grating has a wedge angle that provides slit curvature correction and wherein said light passes through said wedged germanium or zinc selenide grating substrate and is spectrally dispersed by said reflecting immersed grating, and
   a concave reflective secondary mirror focusing said light onto a two-dimensional detector array.

4. An infrared reflective imaging spectrometer apparatus, comprising:
   an entrance slit for directing light,
   a concave reflective primary mirror for reducing the divergence of said light from said entrance slit,
   a wedged germanium or zinc selenide immersed grating dispersing said light,
   and
   a concave reflective secondary mirror focusing said light onto a two-dimensional detector array, wherein the said concave reflective primary and said concave reflective secondary mirror have conic sections or rotational aspheric sections or toric sections.

5. An infrared reflective imaging spectrometer apparatus, comprising:
   an entrance slit for directing light,
   a concave reflective primary mirror for reducing the divergence of said light from said entrance slit,
   a wedged germanium or zinc selenide immersed grating dispersing said light, wherein said wedged germanium or zinc selenide grating is a holographic grating that provides further aberration and distortion correction, and
   a concave reflective secondary mirror focusing said light onto a two-dimensional detector array.

6. An infrared reflective imaging spectrometer apparatus, comprising:
   an entrance slit for directing light,
   a concave reflective primary mirror for reducing the divergence of said light from said entrance slit,
   a wedged germanium or zinc selenide immersed grating dispersing said light, wherein said wedged germanium or zinc selenide grating is a diffraction grating with non-uniform groove spacings, and
   a concave reflective secondary mirror focusing said light onto a two-dimensional detector array.

7. An infrared reflective imaging spectrometer apparatus, comprising:
   an entrance slit for directing light,
   a concave reflective primary mirror for reducing the divergence of said light from said entrance slit,
   a wedged germanium or zinc selenide immersed grating dispersing said light, wherein optical materials for said wedged grating are materials that transmit visible light for operation in the visible spectral region, and
   a concave reflective secondary mirror focusing said light onto a two-dimensional detector array.

8. An infrared reflective imaging spectrometer apparatus, comprising:
   an entrance slit for directing light,
   a concave reflective primary mirror for reducing the divergence of said light from said entrance slit,
   a wedged germanium or zinc selenide immersed grating dispersing said light,
   a concave reflective secondary mirror focusing said light onto a two-dimensional detector array, and
   a lens in front of said detector array to control the field curvature.

9. An infrared reflective imaging spectrometer, comprising:
   an entrance slit for admitting light, a concave reflective primary mirror focusing said light from said entrance slit, a convex reflective secondary mirror diverging said light, a wedged germanium or zinc selenide immersed grating for dispersing said light, said wedged germanium or zinc selenide grating having a wedge angle providing slit curvature correction, wherein said light passes through said wedged germanium or zinc selenide grating to be spectrally dispersed by said reflecting immersed grating, a convex reflective tertiary mirror diverging said light; and a concave reflective quaternary mirror focusing said light onto a two-dimensional detector array.

10. The infrared reflective imaging spectrometer apparatus of claim 9 wherein said wedged germanium or zinc selenide grating has a wedge angle that provides slit curvature correction and wherein said light passes through said wedged germanium or zinc selenide grating substrate and is spectrally dispersed by said reflecting immersed grating.

11. The infrared reflective imaging spectrometer apparatus of claim 9 wherein some or all of said primary, secondary, tertiary and quaternary mirrors have conic sections or rotational aspheric sections or toric sections for further aberration correction.

12. The infrared reflective imaging spectrometer apparatus of claim 9 wherein the said wedged grating includes transmissive grating grooves and is transmissive and wherein said light passes through said grating and is spectrally dispersed by said transmissive grating grooves.

13. The infrared reflective imaging spectrometer apparatus of claim 9 wherein said wedged germanium or zinc selenide grating is a conventional straight grooved grating.

14. The infrared reflective imaging spectrometer apparatus of claim 9 wherein said wedged germanium or zinc selenide grating is a holographic grating that provides further aberration and distortion correction.

15. The infrared reflective imaging spectrometer apparatus of claim 9 wherein said wedged germanium or zinc selenide grating is a diffraction grating with non-uniform groove spacings.

16. The infrared reflective imaging spectrometer apparatus of claim 9 wherein said wedged germanium or zinc selenide grating is a diffraction grating with curved groove spacings that provide further aberration and distortion correction.

17. The infrared reflective imaging spectrometer apparatus of claim 9 wherein said wedged grating includes surfaces and wherein said surface are adapted to receive power for greater distortion and field curvature correction.

18. The infrared reflective imaging spectrometer apparatus of claim 9 wherein said wedged grating includes materials that transmit visible light for operation in the visible spectral region to enhance the transmittance in the near, mid or long wave infrared regions.

19. The infrared reflective imaging spectrometer apparatus of claim 9 wherein optical materials for said wedged grating are materials that transmit visible light for operation in the visible spectral region.

20. The infrared reflective imaging spectrometer apparatus of claim 9 including a lens added in front of said detector array to control the field curvature.

* * * * *